United States Patent
Page

(10) Patent No.: US 7,087,027 B2
(45) Date of Patent: Aug. 8, 2006

(54) DEVICE AND METHOD FOR MONITORING RESPIRATION

(76) Inventor: Thomas C. Page, 30 Prospect Bay Dr. West, Grasonville, MD (US) 21638

( * ) Notice: Subject to any disclaimer, the term of this patent is extended or adjusted under 35 U.S.C. 154(b) by 450 days.

(21) Appl. No.: 10/131,407

(22) Filed: Apr. 22, 2002

(65) Prior Publication Data

US 2003/0199780 A1 Oct. 23, 2003

(51) Int. Cl.
*A61B 5/28* (2006.01)

(52) U.S. Cl. .................................. 600/537; 600/538
(58) Field of Classification Search ................ 600/529, 600/531, 532, 533, 537, 538
See application file for complete search history.

(56) References Cited

U.S. PATENT DOCUMENTS

| | | | |
|---|---|---|---|
| 3,884,219 A | 5/1975 | Richardson et al. | |
| 3,903,876 A | 9/1975 | Harris | |
| 3,999,537 A | 12/1976 | Noiles | |
| 4,289,142 A | 9/1981 | Kearns | |
| 4,306,867 A | 12/1981 | Finze | |
| 4,326,404 A | 4/1982 | Mehta | |
| 4,350,166 A | 9/1982 | Mobarry | |
| 4,366,821 A | 1/1983 | Wittmaier et al. | |
| 4,595,016 A | 6/1986 | Fertig et al. | |
| 4,745,925 A | 5/1988 | Dietz | |
| 4,878,502 A | 11/1989 | Dietz | |
| 5,069,222 A * | 12/1991 | McDonald, Jr. | 600/537 |
| 5,161,541 A * | 11/1992 | Bowman et al. | 600/537 |
| 5,311,875 A | 5/1994 | Stasz | |
| 6,024,089 A | 2/2000 | Wallace et al. | |
| 6,171,258 B1 | 1/2001 | Karakasoglu et al. | |
| 6,575,916 B1 * | 6/2003 | Halleck et al. | 600/528 |

* cited by examiner

*Primary Examiner*—Max F. Hindenburg
*Assistant Examiner*—Navin Natnithithadha
(74) *Attorney, Agent, or Firm*—Levisohm, Berger & Langsam, LLP

(57) ABSTRACT

A system and method are provided to monitor a patient's respiration during and after medical/surgical procedures, as well as in clinical situations wherein the patient is at increased risk for developing central or obstructive respiratory depression and/or apnea. A sensor attached to the patient's face, which monitors nasal and oral air-flows. An electronic monitor analyzes patient respiratory patterns and initiates bedside and/or remote nursing station alarms in real time if and when a clinically significant respiratory event is detected. Respiration is measured by monitoring changes in the acoustic signature of the patient's breath passing over a corrugated or uneven surface, changes in the pressure of an inflatable closed volume of a sensor caused by the changes in temperature of the interior volume caused by the patient breathing over the sensor, or both.

42 Claims, 6 Drawing Sheets

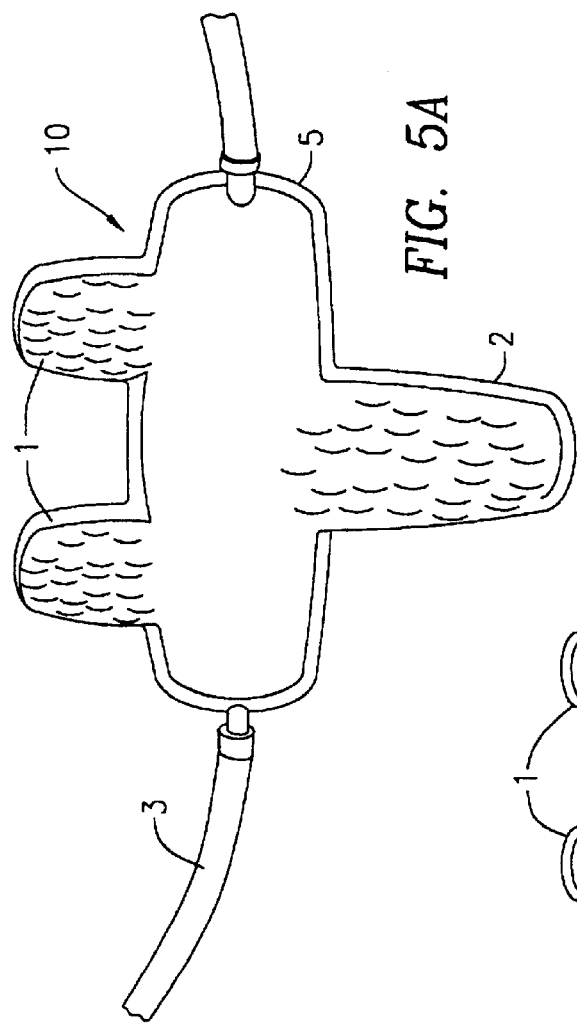
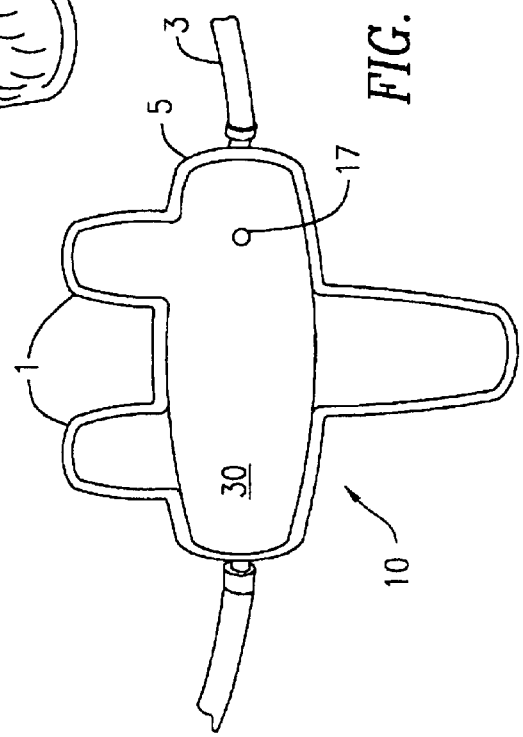
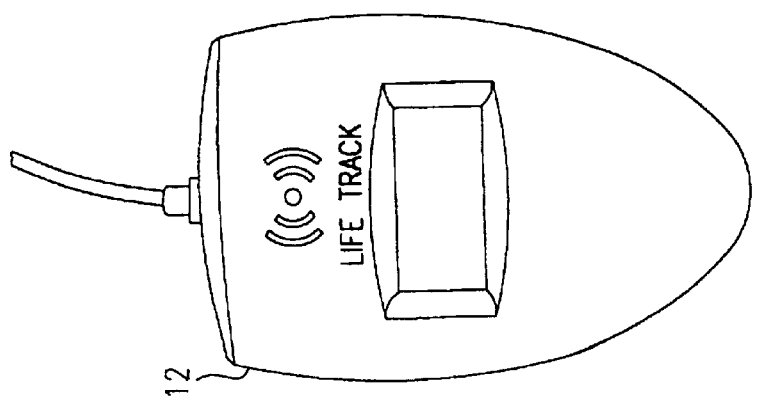
FIG. 5A
FIG. 5B
FIG. 5C

DEVICE AND METHOD FOR MONITORING RESPIRATION

BACKGROUND OF INVENTION

1. Field of Invention

The present invention generally relates to respiratory sensor and alarm technology, and more particularly, relates to a dual mode respiratory airflow sensor and monitoring technology for the detection of any and all potentially life threatening respiratory events.

2. Description of Related Art

It is known in the art to monitor patients susceptible to disorders of the respiratory system, or in critical care settings, to employ respiration sensors and alarm systems. U.S. Pat. No. 4,878,502 issued to Dietz discusses a respiration airflow sensor employing a tube in which a ball is free to move, thereby breaking a beam of light. The ball is forced to move by the flow of air associated with the breathing of the patient. In U.S. Pat. No. 4,745,925 also issued to Dietz, another variation of an opthoelectric inhalation sensor using thin film deposition is discussed. Monitoring of respiration disorders by acoustic sensors is mentioned in U.S. Pat. No. 4,602,644 issued to DeBenedetto et al., and in U.S. Pat. No. 4,595,016 issued to Fertig et al. U.S. Pat. No. 4,366,821 issued to Wittmaier et al. shows a respiration monitoring system, which preferably uses a gas sensor. U.S. Pat. No. 4,350,166 issued to Mobarry shows an infant respiration detector of long wave infrared light which is absorbed by carbon dioxide. When an infant's exhalation (and thus its production of carbon dioxide) is interrupted, an alarm is activated. In U.S. Pat. No. 4,326,404 issued to Mehta, moisture is sensed using a sodium chloride crystal.

U.S. Pat. No. 4,306,867 issued to Krasner shows the use of a pressure sensor. An impedance plethysmograph is employed in U.S. Pat. No. 4,289,142 issued to Kearns. The use of thermoresistive sensors is suggested in U.S. Pat. No. 3,903,876 issued to Harris, U.S. Pat. No. 3,884,219 issued to Richardson et al., and U.S. Pat. No. 3,999,537 issued to Noiles. All of the above methods are complicated and expensive, or else unworkable in a real hospital setting for perioperative patients.

Pulse oximeters are also used on a patient's extremity, typically a finger, which monitor the oxygen content of a patient's blood through non-invasive means. However, a pulse oximeter can only detect hypoxia after the condition has arisen, i.e., after respiratory depression has occurred for a significant period of time.

Other possible solutions (and their associated problems) include capnographic end tidal $CO_2$ monitors (highly accurate but prohibitively expensive), hemodynamic monitors which use Swan Ganz pulmonary artery catheters (expensive and have a high morbidity), and increased physician- or nurse-to-patient ratios (prohibitively expensive and inefficient).

There is thus a need in the field of perioperative healthcare for an inexpensive system and method of monitoring a patient's respiration that are reliable, workable, and practical in the typical perioperative environment.

SUMMARY OF INVENTION

The present invention overcomes the disadvantages found in the prior art by providing a plurality of respiration related signals, derived from different physical phenomena, from a single sensor element fabricated on a single substrate. Moreover, the present invention includes a sensor construction which is less susceptible to interference from the external environment and loss of signal. It is advantageous to monitor multiple sensing channels, provided that care is taken to increase reliability of each channel, so that the overall reliability of the monitoring system is enhanced. In the present invention, all these advantages are achieved by employing a "closed volume/corrugated surface" (CVCS) respiration flow probe, rather then the "open tube" cannula type or the various thermo-sensor approaches described in the Background section above.

The CVCS sensor monitors respiration airflow temperature as reflected by the changes of pressure within a closed, fixed volume in thermal contact with the respiration airflow. By detecting flow-generated acoustical signatures, the invention also monitors airflow when turbulence is generated over the deliberately rough external or front surface of the sensor. Breathing sounds like snoring or coughs can also be monitored as they are picked up through the thin film comprising the external or front surface of the sensor.

In the preferred embodiment, the invention includes a respiration sensor apparatus having a sensor with an inflatable body having an outside surface and an interior volume, disposable between the mouth and nose of a patient. At least one tube in communication with the interior volume extends away from the sensor. A monitor is connected to the second end of the tube and detects respiration of the patient by detecting variations in either pressure within the interior volume or sound waves generated by the patient's respiration flowing over the sensor, or both. These variations may be anticipated variations occurring through normal respiration or abnormal variations indicative of respiratory distress.

Preferably, corrugations or undulations are disposed on the outside surface, so that when the patient breathes over the sensor, the corrugations increase turbulence of the respiratory airflow over the outer surface to thereby increase the level of sound generated by respiration, allowing for better and more accurate detection. The inflatable body preferably includes a bendable inelastic substrate and a plastic inflatable film sealingly attached to the substrate to form the interior volume. A proximal surface of the sensor is disposable against the face of the patient between the nose and mouth. A hole is preferably formed in the proximal surface communicating with the interior volume, so that when the sensor is disposed on the patient's face, the hole is covered and closed by the patient's face. If the sensor loses contact with the patient's face, the hole opens, and the interior volume is in communication with the ambient air; the monitor detects the concomitant change in pressure of the interior volume.

The monitor of the inventive system includes a pressure transducer in communication with the tube for measuring the pressure in the tube and the interior volume. When the patient breathes over the sensor, the breathing causes a change in temperature of the interior volume which in turn causes a change in pressure of the interior volume. The monitor also may include an acoustical transducer in communication with the tube for measuring the sound generated by the patient's breath passing over the inflatable body and conducted via the tube to the monitor. To maintain the pressure inside the interior volume at a higher level than atmospheric pressure, the monitor may further include a pump in communication with the tube providing positive pressure into the tube and the interior volume.

BRIEF DESCRIPTION OF DRAWINGS

The objectives of the present invention and many of the attendant advantages of the present invention can be further appreciated by reference to the following drawings:

FIG. 5A is a front perspective view of a two-tube embodiment of the present invention.

FIG. 5B is a rear perspective view of the embodiment of FIG. 5A.

FIG. 5C is a front perspective view of an embodiment of a monitor of the present invention.

DETAILED DESCRIPTION OF THE PREFERRED EMBODIMENTS

The preferred embodiment of the respiratory sensor is fabricated using lamination and adhesive techniques on a film substrate. The lamination is performed in such a way as to provide the proper physical relationship of the individual sensor parts, which detects the patient's nasal and oral respiration. The sensor is a closed volume or bubble of plastic film with extensions or protrusions extending towards the nostrils and mouth.

Respiration is detected through the change in temperature of the air enclosed in this bubble when ambient room air, inspiratory, and expiratory air flows pass over the sensor. This change in temperature generates a change in pressure in the closed volume largely in accordance with Gay-Lussac's Law, which is:

$$P/T = P'/T' \text{ where } V \text{ is constant} \quad (1)$$

and where P=pressure, T=temperature, V=volume.

These pressure changes are monitored by a pressure sensor in the control box connected to the bubble via at least one tube.

A second respiration input signal is comprised of the noise generated by the flow of air as it passes over the corrugated or uneven surface of the outer or front surface of the sensor. This noise is picked up by a high sensitivity microphone or audio transducer located in the monitor and connected to the bubble by the same at least one tube. This signal benefits from the closed bubble construction, which attenuates ambient noises and thus allows for concise recording and interpretation of respiratory airflow.

The resulting multiple signal respiration detection system may be effectively used as a respiratory alarm that has the benefits of increased sensitivity to respiration variations on the one hand and improved immunity to external interference on the other.

Description will now be given of the invention with reference to the attached figures. These figures are merely exemplary in nature and in no way serve to limit the scope of the invention, which is defined by the claims appearing hereinbelow.

Figure 3:
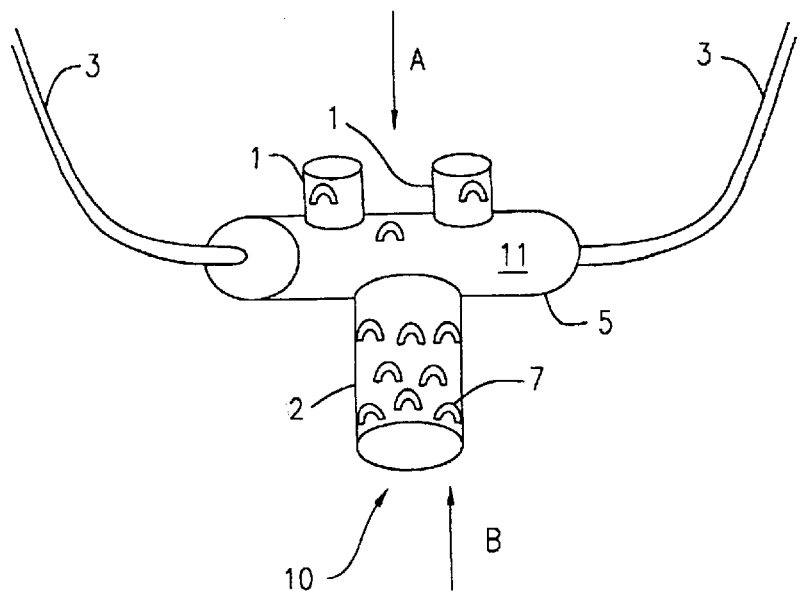
FIG. 3 is a perspective schematic view of a preferred embodiment of a sensor of the present invention.

Referring to FIG. 3, a sensor 10 of the present invention comprises a main body 5. In the preferred embodiment, the sensor 10 is constructed in a two layer laminate design. The base material is a flexible, non-stretching substrate on which a second layer of thin plastic film is laminated. The two layers are attached together only around the edges or the contour of the sensor (as represented in the drawing), forming a closed, leak-free sensor volume. The upper layer must be able to allow for the transmission of heat from the patient's breath passing over the sensor to the interior of the sensor, i.e., it should be non-insulating. Preferably, polyethylene film would serve as an appropriate material, however other polymeric films would also be satisfactory. In a broader sense, any inelastic expandable and contractible material that would allow heat from the patient's breath to be transmitted to the interior volume of the sensor would be appropriate, and the invention contemplates using any such material.

Two protrusions 1 extend from the main body 5 of the sensor 10 upward to monitor nasal airflow, and one larger protrusion 2 extends from the body 5 of the sensor 10 downwards to sense oral airflow. Unlike traditional cannulae used to monitor air pressure changes representative of respiratory airflow, the nasal and oral sensors are not open to the atmosphere, and the entire assembly is airtight and leak-proof. Protrusions 1 encounter air flow from the patient's nose generally in the direction of arrow A, and protrusion 2 encounters air flow from the patient's mouth generally in the direction of arrow B.

Figure 1:
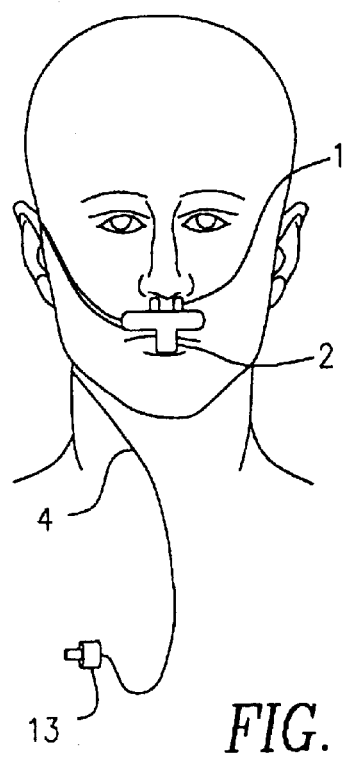
FIG. 1 is a perspective schematic view of a first one-tube embodiment of the invention showing a complete sensor assembly attached to a patient's face.
Figure 2:
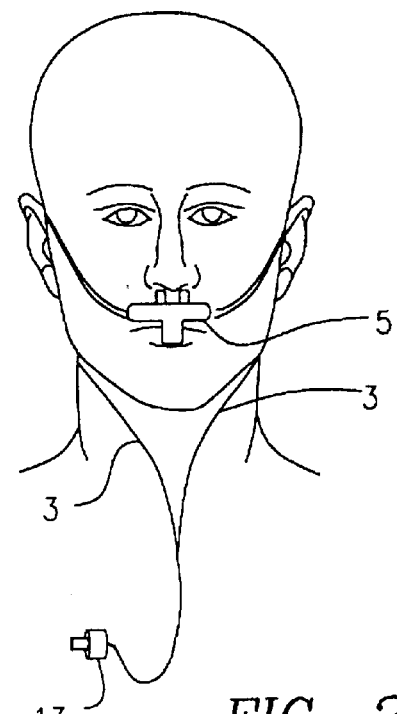
FIG. 2 is a perspective schematic view of a two-tube embodiment of the invention showing a complete sensor assembly attached to a patient's face.
Figure 6A:
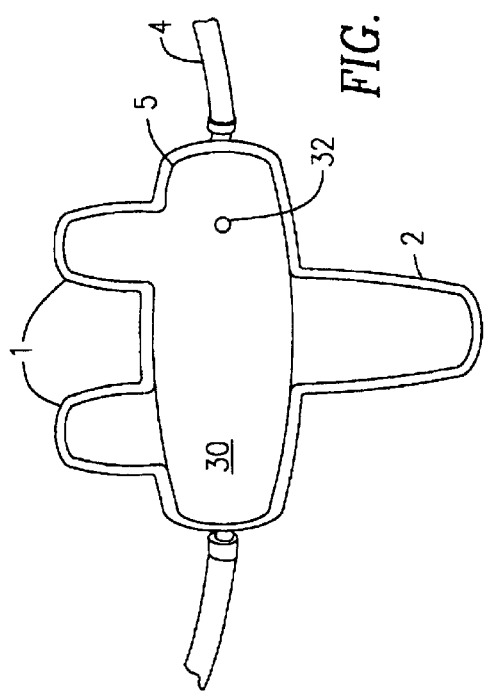
FIG. 6A is a rear perspective view of a one-tube embodiment of the present invention.
Figure 6B:
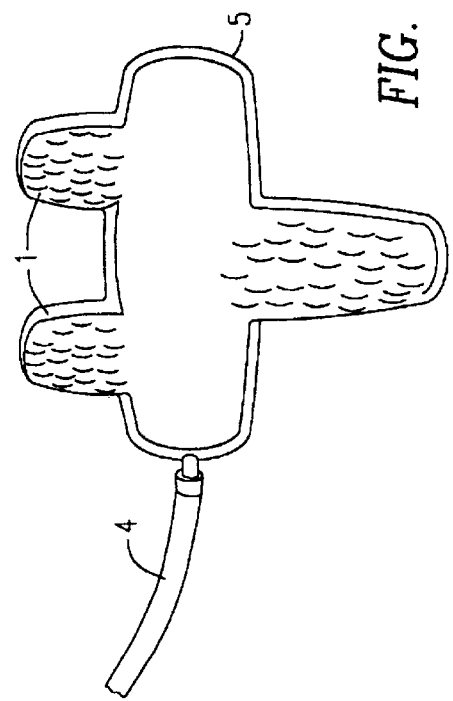
FIG. 6B is a front perspective view of the embodiment of FIG. 6A.
Figure 6C:
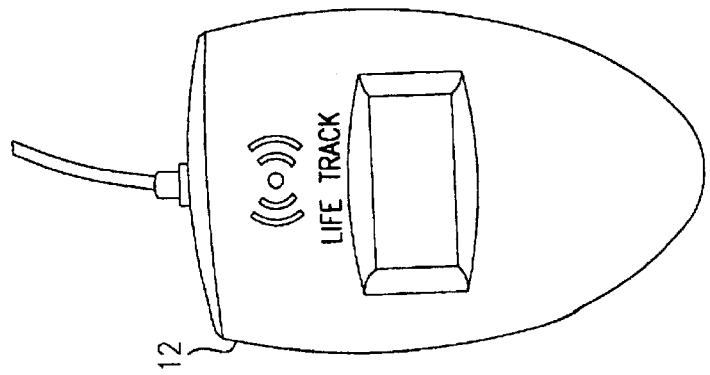
FIG. 6C is a front perspective view of a monitor of the present invention.

Two hollow tubes 3 are mounted and connected inside the closed volume of body 5 for the purpose of signal communication. The hollow tubes 3 protrude respectively from a left end and a right end of the body 5 of the sensor 10. As shown in FIG. 2, the two tubes 3 are preferably routed over the ears and joined under the chin. As shown in FIGS. 1 and 6, an alternative embodiment uses only one hollow tube 4. The one-tube sensor is held in place only by a biocompatible backside adhesive 30. The single tube design is more cost effective, while the two tube design can be used with patients having facial hair, or for patients who have delicate or infected skin at the adhesion site (e.g., after cosmetic surgery on the lips). In either case, it is preferable for the tubes to end in a jack or connector 13 as shown in FIGS. 1 and 2.

Figure 4:
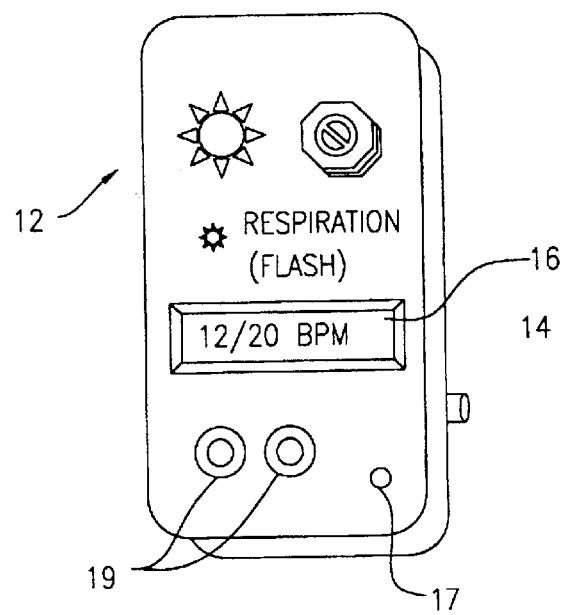
FIG. 4 is a perspective schematic view of an embodiment of a monitor or alarm box of the present invention.
Figure 7:
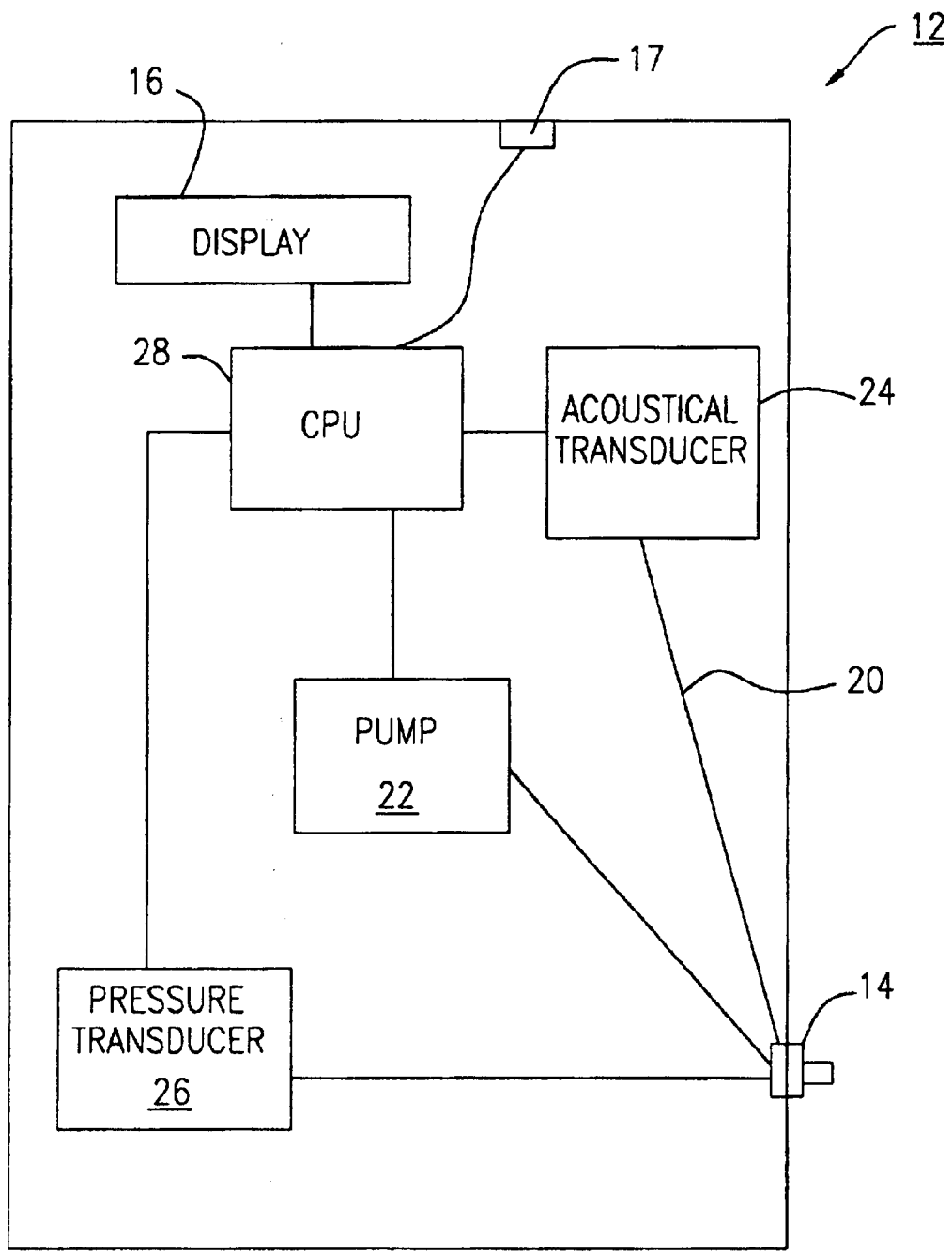
FIG. 7 is a schematic of a monitor of the present invention.

Tubes 3 and/or 4 are connected to monitor 12 via input jack 14 as shown in FIGS. 4 and 7. Monitor 12 may include a display screen 16 which may indicate one or more parameters of the patient's breathing, such as breaths-per-minute, oxygen content, etc. Display 16 may be controlled by one or more buttons 19 provided on the housing of monitor 12 to change either the parameter being displayed, the format of the display, the units (e.g., metric versus English), etc. A jack 17 may be provided to allow external equipment (e.g., headphones, a computer, other diagnostic components, etc.) to be connected to monitor 12 or to allow the data from monitor 12 to be exported or transmitted to a remote location like a central monitoring station (e.g., a nurses' station) or a computer.

As shown schematically in FIG. 7, within the housing of monitor 12 are preferably provided an air pump 22 and a microphone or acoustical transducer 24, both connected to input jack 14 via lines 20. Pump 22 provides positive air pressure to main body 5 via tubes 3 (or tube 4) in order to keep the laminate layer of main body 5 fully inflated.

Pressure transducer 26 monitors the air pressure in sensor 10 via, for example, the pressure in one of the lines 20, and controls pump 22 to stop when the set point pressure is reached. Microphone 24 is utilized to detect the sounds of airflow over the surface of sensor 10 as will be described below.

The hollow tubes 3 or single hollow tube 4 serve several functions. First, they help anchor sensor 10 in place under the nose by serving as lines to hold the sensor. The tubes also communicate the internal pressure inside the sensor's closed volume to pressure transducer 26 within monitor 12. Tubes 3 or 4 also help fill the closed volume in sensor 10 with higher than atmospheric air pressure, generated by pump 22 located in monitor 12. The tubes also transmit the acoustical signals generated by the turbulence of air as it flows over the corrugated outer surface of the sensors, and respiratory sounds picked up though the thin outer membrane of the sensor, to the acoustical transducer 24 in monitor 12.

In the preferred laminated construction embodiment of the sensor, the sensor is manufactured and delivered in a deflated state, where it looks and feels like a thin strip of plastic. This enables the sensor to be easily attached to the patient's upper lip under the nose, conforming to the natural facial contours of the patient. The sensor is attached using an adhesive film or foam 30 (see FIGS. 5 and 6) applied to the backside of the substrate and may be covered with a peelable protective sheet to be removed prior to adhesion to the patient's face.

Once attached to an activated monitor 12, pump 22 inside the monitor 12 starts filling the sensor with air (or another convenient gas) until the internal pressure of the interior volume of sensor 10 is higher than atmospheric pressure; preferably in the range of 2–20 cmH2O. This inflates the sensor giving it its final shape and volume. Pressure transducer 26 inside the monitor 12 continuously records and analyzes the pressure inside the closed sensor volume and stops the pump (either directly or via CPU 28) once the desired pressure is achieved.

As patient-temperature expiratory air and ambient room inspiratory air pass over the sensor, the air sealed inside the closed sensor 10 heats and cools accordingly. These changes in internal temperature translate into changes in pressure as the air expands and contracts in accordance with Guy-Lussac's Law explained above. For a typical temperature change of 2° C. within the internal air cavity (caused by the approximately 20° C. difference between inhaled and exhaled air) and a typical sensor volume of 1 cubic cm, pressure changes are in the range of 5 cmH$_2$O. The monitor's pressure transducer 26 senses these pressure changes and generates a variable signal representative of the respiratory cycle. It should be noted that these pressure changes are representative of temperature, not the result of the air motion over the tips of open cannulae as is the case with other respiratory sensors in the art.

In contrast to all conventional pressure-sensing respiratory monitoring techniques used in the art, this closed volume approach alleviates two major deficiencies. First, the closed volume sensor eliminates the threat of a blocked sensor tip or sensing tube. With patients wearing a conventional sensor for an extended period, and especially if they salivate, have mucus expression or simply try to drink, there is always the risk of a small water or mucus plug clogging the tip of an open sensor or the tube leading to the pressure sensor. Such an occlusion can easily attenuate or completely block the pressure signal, thereby generating a false alarm condition. The same scenario may block the respiratory sound transmission with similar consequences. Because the inventive sensor is closed, there are no openings to become undesirably blocked.

A second problem associated with respiratory pressure sensors is inadequate pickup of oral airflow. In contrast to nasal airflow, which is restricted to a narrow and well-defined route and running through a tube which generates considerable pressure drop even at low flow states, oral airflow may emanate from the mouth at different locations and angles while generating relatively low pressure changes. In addition, adding another opening for oral flow pressure pickup to the standard conventional nasal cannula design deteriorates nasal flow pressure signatures because there is considerable leak through the oral opening when the patient breathes through their nose only. With the inventive sensor, due to its closed volume, the sensor translates temperature changes directly into pressure changes, thereby eliminating all above-referenced drawbacks.

Additionally, unlike all other thermal sensors known in the art, which rely on electrical components like thermistors, diodes or piezo elements for temperature sensing to monitor temperature changes associated with respiration, the inventive sensor 10 is completely without any metal or other electrically-conductive components. This allows for it to be used inside MRI magnets and similar diagnostic high-energy fields. The sensor 10 is also radio-transparent, eliminating possible interference in CT and X-ray applications.

As shown in FIG. 3, the outer surface 11 of sensor 10 is preferably made with multiple miniature bumps, protrusions, or corrugations 7 each preferably 0.1 to 2 mm high and spaced 0.2 to 2 mm apart, or in the form of elongated ridges of comparable dimensions positioned perpendicular to the expected direction of airflow. The same design applies to the one-piece molded or inflated tube embodiment of the invention, wherein these bumps can be formed on the external surface of the tube in the molding/inflating process.

When the air flows over this uneven or corrugated surface, a significant amount of turbulence is produced. This turbulence generates a high frequency hiss, normally at 2 Khz and above, which can be easily picked up by the acoustic transducer and isolated from the background noises associated with the patient's speech or ambient room noises also picked up by the sensor. The amplitude and frequency characteristics of this turbulence-generated signal are proportional to the speed and volume of air flowing over the sensors, and are independent of temperature. The acoustic transducer 24 picks up this sonic data from, e.g., line 20 from input jack 14 and transmits it to CPU 28. Software analyzes the signal to derive a second value representative of the patient's respiratory airflow pattern. It is important to note that this signal is the same for both inhalation and exhalation, which means that proper interpretation of the patient's respiratory health and/or compromise is independent of pressure signal to distinguish between various respiratory phases. While temperature signal is largely not proportional to respiratory volume, the respiration volume may be calculated from the patient's noise turbulence signal.

Both signals from the temperature/pressure channel and from the noise analysis channel are combined in the algorithm of CPU 28 to arrive at a highly precise determination of normal or abnormal respiration, which can be compared to critical values within the monitor pre-set by medical personnel such as a biomedical engineering technician or the physician treating the patient. Preset values may be input to monitor 12 via buttons 19, via jack 17 electronically, or may be preset by the manufacturer ahead of time. Other means of programming the monitor 12, such as by wireless infrared, ultrasonic, or radio frequency signals, are contemplated as well. Alarms will be activated by a similar user selected pre-set function, wherein alarms will sound at the patient's bedside, and/or optionally at the central nursing station. In special cases where the physician desires the patient to be alerted to this situation, bedside alarms will incorporate an option for an assortment of wildly varying alarm sounds, so that the patient will be less likely to habituate the sound of one given alarm signature. Alarms can be reset to be activated automatically if certain parametric thresholds are exceeded or not met, for example (but not limited to) i) rate fluctuations in respiration, ii) increased inhalation, iii) decreased inhalation, iv) exhalation time ratios, and v) fluctuations in respiratory acoustic signatures.

Pressure sensor 26 may also serve to verify that the sensor 10 is properly connected to the system, attached on the patient and is in good working condition. The higher than atmospheric air pressure within the closed sensor volume is continuously measured. When a leak develops due to either a break in the sensor's body because it was used before or due to a production defect, or the disconnection of tube 3, 4 from monitor 12, the device issues both displayed and audible "sensor error" alarms, which sounds significantly different from the patient/central nursing station apnea alarm. The same feature is used to verify that sensor 10 remains properly secured to the patient's face. During sensor placement on the patient, the adhesive protective cover is removed from the backside of the sensor, which may preferably expose a small hole 32 formed in the sensor substrate, which is in communication with the interior volume of sensor 10. If for any reason the sensor is removed (or even slightly peels off) inadvertently or by mistake from the patient's face, hole 32 is exposed to normal atmospheric pressure and a leak forms, which activates the "sensor error" alarms.

Figure 8:
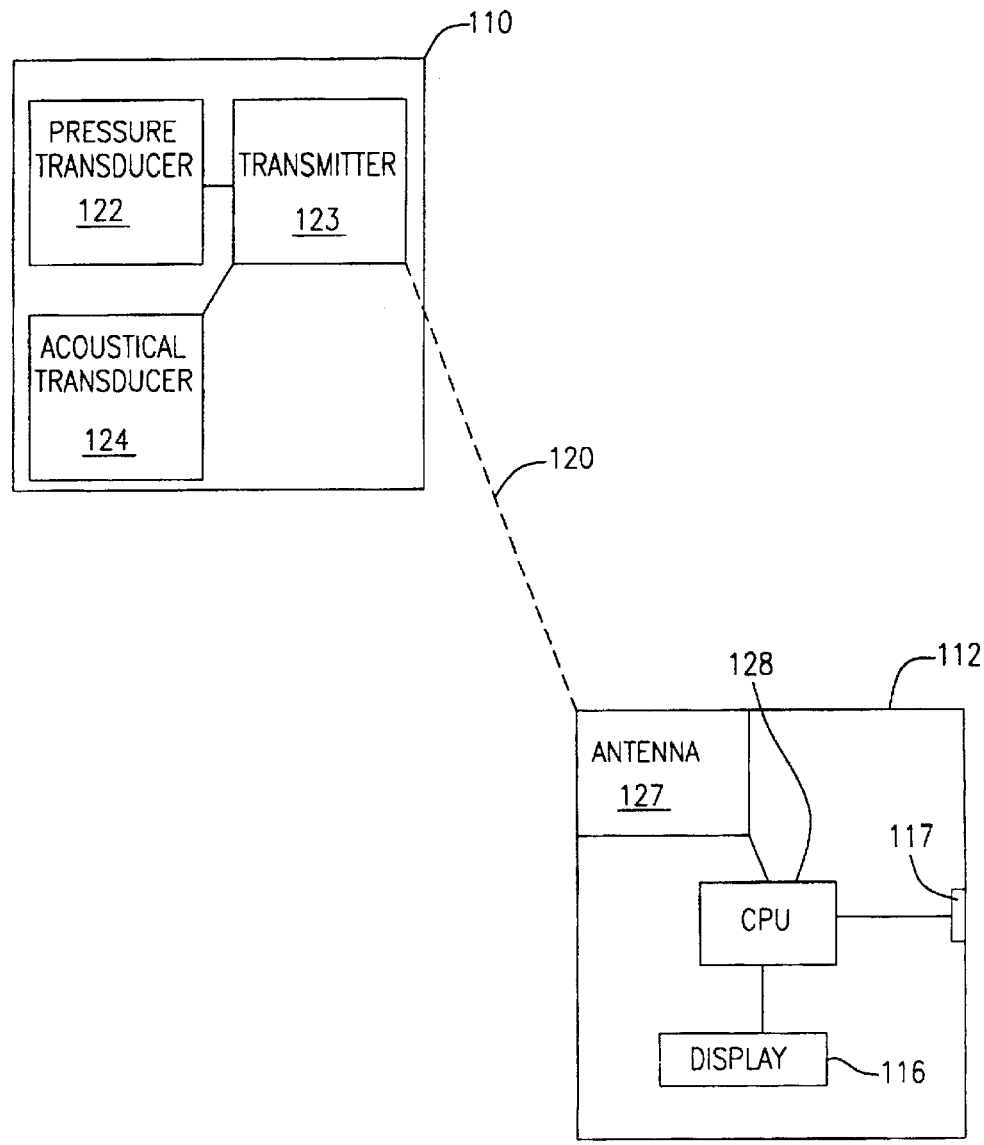
FIG. 8 is a schematic of an alternative embodiment of the inventive sensor and monitor.

The invention is not limited to the above description. For example, the sensor need not be physically connected to the monitor but may employ a wireless means of communication, e.g., an RF transmission of data. In such an embodiment, as shown in FIG. 8, the main balloon of sensor 110 may be sealed at manufacture and may include an internal pressure transducer 122 similar to the one shown internal to monitor 12 in FIG. 7. Sensor 110 may also include acoustical transducer 124 similar to that shown in FIG. 7. An RF transmitter 123 can transmit the data picked up by pressure transducer 122 and acoustical transducer 124. In this embodiment, monitor 112 includes an antenna or receiver 127 which receives signal 120 transmitted by sensor 110. CPU 128 is connected to receiver or antenna 127 and processes the signals in a manner similar to that of CPU 28. A display 116 is also connected to CPU 128 and shows the information so processed. CPU can also be connected to an external jack 117 to import or export data as above.

Further, instead of providing a data port such as jacks 17 or 117, the inventive monitor could be hardwired into a larger data-collecting, computing, or monitoring system.

The invention is not limited to the above description but rather is defined by the claims appearing hereinbelow. Modifications to the above description that include that which is known in the art are well within the scope of the contemplated invention.

What is claimed is:

1. A respiration sensor apparatus comprising:
    a sensor capable of sensing relative high frequency acoustic signals with a frequency of at least 2 Khz, including an inflatable body having an outside surface and an interior volume, disposable between the mouth and nose of a patient;
    at least one tube having two ends, one end being in communication with said interior volume and extending from said sensor; and
    a monitor, connected to said second end of said tube, detecting respiration of the patient by detecting variations in at least one of a) pressure within said interior volume, and b) sound waves generated by the patient's respiration flowing over said sensor.

2. A respiration sensor apparatus according to claim 1, further comprising corrugations disposed on said outside surface, wherein when the patient breathes over said sensor, said corrugations increase turbulence of the respiratory airflow over said outer surface to thereby increase the amount of sound generated by respiration.

3. A respiration sensor apparatus according to claim 1, said inflatable body further comprising:
    a bendable inelastic substrate; and
    a plastic inflatable film sealingly attached to said substrate to form said interior volume.

4. A respiration sensor apparatus according to claim 1, said inflatable body having a proximal surface disposable against the face of the patient, further comprising a hole formed in said proximal surface communicating with said interior volume,
    wherein when said sensor is disposed on the patient's face, said hole is covered and closed by the patient's face.

5. A respiration sensor apparatus according to claim 4, wherein if said sensor loses contact with the patient's face, said hole opens, and said interior volume becomes in communication with the ambient air, and said monitor detects the concomitant change in pressure of the interior volume.

6. A respiration sensor apparatus according to claim 4, further comprising an adhesive disposed on said proximal surface for adhering said sensor to the patient's face.

7. A respiration sensor apparatus according to claim 5, said monitor further comprising a pump in communication with said tube providing positive pressure into said tube and said interior volume.

8. A respiration sensor apparatus according to claim 1, said monitor further comprises a pressure transducer in communication with said tube for measuring the pressure in said tube and said interior volume.

9. A respiration sensor apparatus according to claim 8, wherein when the patient breathes over said sensor, the breathing causes a change in temperature of said interior volume which in turn causes a change in pressure of said interior volume.

10. A respiration sensor apparatus according to claim 9, said monitor further comprising a central processing unit (CPU), connected to said pressure transducer, analyzing pressure readings detected by said pressure transducer and determining a rate of respiration of the patient from the pressure readings.

11. A respiration sensor apparatus according to claim 10, further comprising means for transmitting respiration data from said CPU to a remote location.

12. A respiration sensor apparatus according to claim 1, said monitor further comprises an acoustical transducer in communication with said tube for measuring the sound generated by the patient's breath passing over said inflatable body and conducted via said tube to said monitor.

13. A respiration sensor apparatus according to claim 12, said monitor further comprising a central processing unit (CPU), connected to said acoustical transducer, analyzing acoustical readings detected by said acoustical transducer and determining a rate of respiration of the patient from the acoustical readings.

14. A respiration sensor apparatus according to claim 13, further comprising means for transmitting respiration data from said CPU to a remote location.

15. A respiration sensor apparatus according to claim 1, said monitor further comprising:
   a pressure transducer in communication with said tube for measuring the pressure in said tube and said interior volume; and
   an acoustical transducer in communication with said tube for measuring the sound generated by the patient's breath passing over said inflatable body and conducted via said tube to said monitor,
   wherein when the patient breathes over said sensor, the breathing causes a change in temperature of said interior volume which in turn causes a change in pressure of said interior volume.

16. A respiration sensor apparatus according to claim 15, said monitor further comprising a central processing unit (CPU), connected to said pressure transducer and said acoustical transducer, analyzing pressure readings detected by said pressure transducer and acoustical readings detected by said acoustical transducer and determining a rate of respiration of the patient from the pressure and acoustical readings.

17. A respiration sensor apparatus according to claim 16, further comprising means for transmitting respiration data from said CPU to a remote location.

18. A respiration sensor apparatus according to claim 1, said monitor further comprising a pump in communication with said tube providing positive pressure into said tube and said interior volume.

19. A respiration sensor apparatus according to claim 1, said monitor further comprising an alarm, wherein if the variations are not detected over a predetermined period of time, said alarm is activated.

20. A respiration sensor apparatus according to claim 1, said at least one tube further comprising two of said tubes attached to opposite ends of said sensor, each of said tubes being respectively bendable around the patient's ears to facilitate retention of said sensor on the patient's face.

21. A respiration sensor apparatus according to claim 1, said sensor further comprising:
   at least one first projection extending upwardly from said inflatable body to substantially correspond to at least one of the patient's nostrils; and
   at least one second projection extending downwardly from said inflatable body to substantially correspond to the patient's mouth.

22. A sensor for detecting a person's respiration, comprising: an inflatable body having an outside surface and an interior volume, dimensioned to be disposable between the mouth and nose of a patient; and
   corrugations disposed on said outside surface, wherein when the patient breathes over said sensor, said corrugations serving to sense a change in turbulence of the respiratory airflow over said outer surface to thereby amplify the sound generated by respiration.

23. A respiration sensor according to claim 22, said inflatable body further comprising:
   a bendable inelastic substrate; and
   a plastic inflatable film sealingly attached to said substrate to form said interior volume.

24. A respiration sensor according to claim 22, said inflatable body having a proximal surface disposable against the face of the patient, further comprising a hole formed in said proximal surface communicating with said interior volume,
   wherein when said sensor is disposed on the patient's face, said hole is covered and closed by the patient's face.

25. A respiration sensor according to claim 24, wherein if said sensor loses contact with the patient's face, said hole is uncovered and opens and said interior volume becomes in communication with the ambient air and the pressure of the interior volume correspondingly changes.

26. A respiration sensor according to claim 24, further comprising an adhesive disposed on said proximal surface for adhering said sensor to the patient's face.

27. A respiration sensor according to claim 22, wherein when the patient breathes over said sensor, the breathing causes a change in temperature of said interior volume which in turn causes a change in pressure of said interior volume.

28. A respiration sensor according to claim 22, said sensor further comprising a communication with said interior volume accepting positive pressure into said interior volume from an external source.

29. A respiration sensor according to claim 28, wherein said sensor is connectable to a multi-variable monitor via said port.

30. A respiration sensor according to claim 22, said sensor further comprising:
   at least one first projection extending upwardly from said inflatable body to substantially correspond to at least one of the patient's nostrils; and
   at least one second projection extending downwardly from said inflatable body to substantially correspond to the patient's mouth.

31. A respiration sensor according to claim 30, said first and second projections being closed structures, wherein said corrugations extend over said first and second projections.

32. A method for monitoring a person's respiration comprising the steps of:
   passing a patient's breath over a corrugated surface of a sensor to create air turbulence;
   generating a measurable acoustic signature with varying frequency and intensity proportional to respiratory air flow and volume; and
   monitoring the acoustic signature with an appropriate pickup.

33. A method for monitoring a person's respiration according to claim 32, further comprising the steps of:
   providing a closed interior volume in the sensor;
   detecting changes in pressure in the interior volume of the sensor caused by changes in temperature of the interior volume which are caused by the person's respiration passing over the sensor.

34. A method for monitoring a person's respiration according to claim 33, further comprising the steps of:
   providing higher than atmospheric pressure inside the closed interior volume.

35. A method for monitoring a person's respiration according to claim 34, further comprising the steps of:
   deflating the interior volume when not in use.

36. A method for monitoring a person's respiration according to claim 34, wherein the air pressure in the interior volume is 2–20 cm $H_2O$.

37. A method for monitoring a person's respiration according to claim 33, further comprising the steps of:
   analyzing pressure and acoustic data collected from the sensor and determining a rate of respiration from the data.

38. A method for monitoring a person's respiration according to claim 37, further comprising the steps of:

transmitting the data to a remote location for viewing by a healthcare professional.

39. A method for monitoring a person's respiration according to claim 33, further comprising the steps of:

monitoring respiratory signals from at least one of a pressure sensor and an acoustic transducer to determine patient respiratory condition; and automatically activating an alarm if respiratory parameters fall outside user selectable thresholds including at least one of i) rate fluctuations in respiration, ii) increased inhalation, iii) decreased inhalation iv) exhalation/inhalation time ratios, and v) fluctuations in respiratory acoustic signatures.

40. A method for monitoring a person's respiration according to claim 39, further comprising the step of varying the sounds of the alarm so that the patient will not become complacent to the sound of a single alarm signature.

41. A method for monitoring a person's respiration according to claim 32, further comprising the steps of:

activating an alarm if interior volume pressure drops by a predetermined value over a predetermined period of time.

42. A method for monitoring a person's respiration according to claim 41, further comprising the steps of:

providing a hole in the sensor in communication with the interior volume of the sensor;

covering and closing the hole by placing the sensor on the patient's face, wherein if the sensor loses contact with the patient's face, the hole is uncovered and opens and said alarm is activated.

* * * * *